(12) United States Patent
Adelson (10) Patent No.: US 10,449,116 B2
(45) Date of Patent: Oct. 22, 2019

(54) FILM DISPENSING DEVICE

(71) Applicant: Resolve Digital Health Inc., Toronto (CA)

(72) Inventor: Robert Adelson, Vaughn (CA)

(73) Assignee: Resolve Digital Health Inc., Toronto (CA)

( * ) Notice: Subject to any disclaimer, the term of this patent is extended or adjusted under 35 U.S.C. 154(b) by 0 days.

(21) Appl. No.: 16/020,453

(22) Filed: Jun. 27, 2018

(65) Prior Publication Data

US 2018/0369066 A1 Dec. 27, 2018

Related U.S. Application Data

(60) Provisional application No. 62/525,557, filed on Jun. 27, 2017.

(51) Int. Cl.

| | |
|---|---|
| *A61J 1/00* | (2006.01) |
| *G16H 20/13* | (2018.01) |
| *A61K 9/70* | (2006.01) |
| *A61J 7/00* | (2006.01) |
| *A61J 3/07* | (2006.01) |

(52) U.S. Cl.
CPC .............. *A61J 1/00* (2013.01); *A61J 7/0076* (2013.01); *A61K 9/7023* (2013.01); *G16H 20/13* (2018.01); *A61J 3/078* (2013.01); *A61J 2200/30* (2013.01); *A61M 2207/10* (2013.01)

(58) Field of Classification Search
None
See application file for complete search history.

(56) References Cited

U.S. PATENT DOCUMENTS

| | | | | |
|---|---|---|---|---|
| 7,540,225 | B2 * | 6/2009 | Lee | B65H 35/0026 156/323 |
| 8,322,262 | B2 * | 12/2012 | Ryu | B65H 37/005 221/30 |
| 2004/0159668 | A1 * | 8/2004 | Vasiadis | B65G 47/1457 221/268 |
| 2006/0243739 | A1 * | 11/2006 | Sherman | A47K 10/22 221/309 |
| 2009/0200330 | A1 * | 8/2009 | Giraud | B65D 83/0829 221/46 |

(Continued)

*Primary Examiner* — Gene O Crawford
*Assistant Examiner* — Ayodeji T Ojofeitmi
(74) *Attorney, Agent, or Firm* — Blake, Cassels & Graydon LLP; Santosh K. Chari (57) ABSTRACT

Aspects of the present disclosure relate to a dispensing device capable of storing and dispensing strips/films. The dispensing device can deliver films of preselected length providing a predetermined medication dose, when required by user making it convenient for user to store, carry and administer the required doses. The dispensing device can allow retrieval and application of strips with minimal manipulation, permitting single-hand operation, thereby maintaining sterility of the strips/films. The dispenser can hold a pharmaceutical or herbal formulation on a suitable delivery material such as a film in roll form or cartridge form. The roll or the cartridge can last for number of doses sufficient for few days thus enabling a user to carry his medicine requirement in a convenient manner. Further, it provides hygienic storage and offers consistent and precise dispensing without user having to touch the thin film strip.

19 Claims, 8 Drawing Sheets

(56) References Cited

U.S. PATENT DOCUMENTS

2009/0277923 A1\* 11/2009 Funke .............. G01N 33/48757
            221/154
2013/0240554 A1\* 9/2013 Strahlin ................ A47K 10/24
            221/1

\* cited by examiner

FILM DISPENSING DEVICE

TECHNICAL FIELD

The present disclosure relates to the technical field of dispensers. In particular, the present disclosure relates to a film dispensing device capable of delivering strips of preselected length providing a predetermined medication dose, when required by user making it convenient for user to store, carry and administer the required doses. The dispensing device allows retrieval and application of strips with minimal manipulation, permitting single-hand operation, thereby maintaining sterility of the strips/films.

BACKGROUND

Background description includes information that may be useful in understanding the present invention. It is not an admission that any of the information provided herein is prior art or relevant to the presently claimed invention, or that any publication specifically or implicitly referenced is prior art.

Transdermal strip is a medicated adhesive strip that is placed on skin to deliver a specific dose of medication through the skin. Transdermal strip contains one more medications prescribed to patient and is designed in such a way that the medication permeates patient's skin in a controlled fashion thus attaining more steady levels of the medication in the body. Transdermal strips are also used to heal minor wounds and abrasions to skin's surface. Transdermal strips are customarily packaged individually in a protective covering which needs to be removed before use, i.e. before application of the strips on patient's skin. Removal of the protective covering typically requires extensive manipulation, using two hands, and consequently the sterility or cleanliness of the strips is compromised.

A variety of dispensing devices for storing and automatically dispensing adhesive transdermal strips have been developed in the art to overcome the disadvantages associated with accessing a transdermal strip for topical use. Such dispensing devices actuate the dispensing of adhesive transdermal strip by mechanical means or by electronic means. Despite efforts to date, the existing dispensing devices fail entirely to provide provisions for monitoring critical clinical informations including dose size, timing and frequency of doses administered to a patient, and for analyzing the monitored data in a way that would be useful for either therapy or in a clinical setting. Furthermore, there is no mechanism to monitor and record the symptoms before and after a dose has been administered to a patient, and communicate the same to doctors, pharmaceutical companies, drug stores or caregiver in real time to enhance patient clinical care. Therefore, pharmaceutical companies, doctors or caregivers have no means to remain connected with the user to learn about the effectiveness of the medication.

There is therefore a need in the art to provide a film dispensing device capable of delivering strips of preselected length providing a predetermined medication dose, when required by user making it convenient for user to store, carry and administer the required doses. Need was also felt of a dispensing device that allows retrieval and application of strips with minimal manipulation, permitting single-hand operation, thereby maintaining sterility of the strips/films. The present disclosure satisfies the existing needs, as well as others, and generally overcomes the deficiencies found in the conventional film dispensing devices.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all groups used in the appended claims.

OBJECTS OF THE INVENTION

An object of the present disclosure is to provide a film dispensing device that generally overcomes the deficiencies found in the conventional dispensing device.

Another object of the present disclosure is to provide a film dispensing device for dispensing of a film.

Another object of the present disclosure is to provide a film dispensing device for dispensing of a film impregnated with at least one active ingredient.

Another object of the present disclosure is to provide a film dispensing device capable of delivering an active agent in a controlled manner.

Another object of the present disclosure is to provide a film dispensing device capable of monitoring and electronically recording medication doses administered to a patient Another object of the present disclosure is to provide a cartridge for storing at least one film and dispensing a single film at a time.

Another object of the present disclosure is to provide a film dispensing device for dispensing of a film without any human intervention.

Another object of the present disclosure is to provide a film dispensing device capable of delivering an active agent without any overdose or under-dose.

Another object of the present disclosure is to provide a film dispensing device capable of delivering an active agent under sterile condition.

Another object of the present disclosure is to provide a film dispensing device capable of delivering an active agent without any gastro-intestinal discomfort.

Another object of the present disclosure is to provide a film dispensing device that is easy to operate.

Another object of the present disclosure is to provide a portable film dispensing device.

Another object of the present disclosure is to provide a film dispensing device that requires user approval for dispensing of a film.

SUMMARY OF THE INVENTION

The present disclosure relates to the technical field of dispensers. In particular, the present disclosure relates to a film dispensing device capable of delivering strips of preselected length providing a predetermined medication dose, when required by user making it convenient for user to store, carry and administer the required doses. The dispensing device allows retrieval and application of strips with minimal manipulation, permitting single-hand operation, thereby maintaining sterility of the strips/films.

Aspects of the present disclosure relate to a dispensing device capable of storing and dispensing strips. The dispensing device can deliver strips of preselected length providing a predetermined medication dose, when required by user making it convenient for user to store, carry and administer the required doses. The dispensing device can allow retrieval and application of strips with minimal manipulation, permitting single-hand operation, thereby maintaining sterility of the strips/films. The dispenser can hold a pharmaceutical or herbal formulation on a suitable delivery material such as a film in roll form or cartridge form. The roll or the cartridge can last for number of doses sufficient for few days thus enabling a user to carry his medicine requirement in a convenient manner. Further, it provides hygienic storage and offers consistent and precise dispensing without user having to touch the thin film strip.

An aspect of the present disclosure provides a film dispensing device, said device comprising: a housing defining a dispensing orifice; a cartridge for storing at least one film, said cartridge comprising: a chamber to hold said at least one film therewithin, said chamber defined by base, front wall, rear wall and a plurality of side walls of said cartridge, wherein said front wall defines an opening to allow ejection of a single film out of said at least one film, and wherein said base defines a slit along its longitudinal surface; and a tab assembly slidably engaged with said chamber, said tab assembly comprising: a carrier strip defining a film engagement arm extending at an angle relative to longitudinal axis of the carrier strip; and a tab affixed to said carrier strip, said tab extending at an angle relative to the longitudinal axis of said carrier strip; and a driving unit configured to engage with said tab assembly, wherein said driving unit, upon actuation, forces said tab to move along the slit to eject said single film from the opening.

In an embodiment, the driving unit comprises a tab engagement arm, a track, and a motor. In an embodiment, the device further comprises a film carrier track configured to convey said ejected film from said opening to the dispensing orifice for dispensation thereof to a user. In an embodiment, the opening is matingly engaged with said dispensing orifice to allow dispensation of said ejected single film from the dispensing orifice. In an embodiment, the cartridge further comprises a biasing member defined along a wall opposite to said base to urge said at least one film towards said carrier strip. In an embodiment, length of said carrier strip is short as compared to length of said at least one film. In an embodiment, the carrier strip is at an angle relative to longitudinal axis of said base. In an embodiment, the carrier strip is tapered towards said opening. In an embodiment, the device further comprises a sensor configured to detect any or a combination of number of the ejected film and quality of the ejected film. In an embodiment, the base further comprises a lug to blockingly engage with said carrier strip. In an embodiment, the device further comprises a lug engagement arm, that upon actuation of the device movingly disengage said lug from said carrier strip. In an embodiment, the at least one film comprises a multilayered film. In an embodiment, the multi-layered film comprises any or a combination of a backing layer, a protective layer, an adhesive layer and a carrier layer. In an embodiment, the carrier layer comprises a film impregnated with any or a combination of at least one pharmaceutical agent, at least one herbal ingredient, at least one nutraceutical and at least one cosmetic agent.

Another aspect of the present disclosure provides a cartridge for storing at least one film and dispensing a single film at a time, said cartridge comprising: a chamber to hold said at least one film therewithin, wherein said chamber is defined by a base, front wall, rear wall and a plurality of side walls of said cartridge, and wherein said front wall defines an opening to allow ejection of said single film, further wherein said base defines a slit along its longitudinal surface; and a tab assembly slidably engaged with said chamber, wherein said tab assembly comprises: a carrier strip defining a first surface to be mateably engaged with said at least one film and a second surface opposite to said first surface, wherein said carrier strip defines a film engagement arm extending at an angle relative to longitudinal axis of the carrier strip; and a tab affixed to said carrier strip at its second surface, said tab extending at an angle relative to the longitudinal axis of said carrier strip.

In an embodiment, the cartridge further comprises a biasing member defined along a wall opposite to said base to urge said at least one film towards said carrier strip. In an embodiment, length of said carrier strip is short as compared to length of said at least one film. In an embodiment, the tab extends from the slit upon engagement of said tab assembly with said chamber. In an embodiment, the carrier strip is at an angle relative to longitudinal axis of said base. In an embodiment, the carrier strip is tapered towards said opening.

In an embodiment, the dispensing device can incorporate smart features to enable record keeping in respect of timing, dose size, frequency of doses and symptoms before and after a prescribed dose. The maintained records can help in allowing doctors and patients to gain a better understanding of how the medication is functioning to develop a customized treatment program. In an embodiment, the dispenser can incorporate a display screen configured to display symptoms before and after a prescribed dose has been administered to a patient.

In an embodiment, the dispensing device can further incorporate means to communicate data in real time or on as required basis to various stakeholders such as doctor, care giver, drug stores, pharmaceutical companies etc. The means for communication can be a wireless communication means that can enable data transfer from the dispenser to external functional units or networks. Communication between the dispenser and external functional units or networks may be accomplished through any suitable communication channels such as Bluetooth, Wi-Fi, GSM communication means such as 3G etc.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DETAILED DESCRIPTION

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Unless the context requires otherwise, throughout the specification which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The headings and abstract of the invention provided herein are for convenience only and do not interpret the scope or meaning of the embodiments.

Various terms as used herein. To the extent a term used in a claim is not defined below, it should be given the broadest definition persons in the pertinent art have given that term as reflected in printed publications and issued patents at the time of filing.

The present disclosure relates to the technical field of dispensers. In particular, the present disclosure relates to a film dispensing device capable of delivering strips of preselected length providing a predetermined medication dose, when required by user making it convenient for user to store, carry and administer the required doses. The dispensing device allows retrieval and application of strips with minimal manipulation, permitting single-hand operation, thereby maintaining sterility of the strips/films.

Aspects of the present disclosure relate to a dispensing device capable of storing and dispensing strips. The dispensing device can deliver strips of preselected length providing a predetermined medication dose, when required by user making it convenient for user to store, carry and administer the required doses. The dispensing device can allow retrieval and application of strips with minimal manipulation, permitting single-hand operation, thereby maintaining sterility of the strips/films. The dispenser can hold a pharmaceutical or herbal formulation on a suitable delivery material such as a film in roll form or cartridge form. The roll or the cartridge can last for number of doses sufficient for few days thus enabling a user to carry his medicine requirement in a convenient manner. Further, it provides hygienic storage and offers consistent and precise dispensing without user having to touch the thin film strip.

An aspect of the present disclosure provides a film dispensing device, said device comprising: a housing defining a dispensing orifice; a cartridge for storing at least one film, said cartridge comprising: a chamber to hold said at least one film therewithin, said chamber defined by base, front wall, rear wall and a plurality of side walls of said cartridge, wherein said front wall defines an opening to allow ejection of a single film out of said at least one film, and wherein said base defines a slit along its longitudinal surface; and a tab assembly slidably engaged with said chamber, said tab assembly comprising: a carrier strip defining a film engagement arm extending at an angle relative to longitudinal axis of the carrier strip; and a tab affixed to said carrier strip, said tab extending at an angle relative to the longitudinal axis of said carrier strip; and a driving unit configured to engage with said tab assembly, wherein said driving unit, upon actuation, forces said tab to move along the slit to eject said single film from the opening.

In an embodiment, the driving unit comprises a tab engagement arm, a track, and a motor. In an embodiment, the device further comprises a film carrier track configured to convey said ejected film from said opening to the dispensing orifice for dispensation thereof to a user. In an embodiment, the opening is matingly engaged with said dispensing orifice to allow dispensation of said ejected single film from the dispensing orifice. In an embodiment, the cartridge further comprises a biasing member defined along a wall opposite to said base to urge said at least one film towards said carrier strip. In an embodiment, length of said carrier strip is short as compared to length of said at least one film. In an embodiment, the carrier strip is at an angle relative to longitudinal axis of said base. In an embodiment, the carrier strip is tapered towards said opening. In an embodiment, the device further comprises a sensor configured to detect any or a combination of number of the ejected film and quality of the ejected film. In an embodiment, the base further comprises a lug to blockingly engage with said carrier strip. In an embodiment, the device further comprises a lug engagement arm, that upon actuation of the device movingly disengage said lug from said carrier strip. In an embodiment, the at least one film comprises a multi-layered film. In an embodiment, the multi-layered film comprises any or a combination of a backing layer, a protective layer, an adhesive layer and a carrier layer. In an embodiment, the carrier layer comprises a film impregnated with any or a combination of at least one pharmaceutical agent, at least one herbal ingredient, at least one nutraceutical and at least one cosmetic agent.

Another aspect of the present disclosure provides a cartridge for storing at least one film and dispensing a single film at a time, said cartridge comprising: a chamber to hold said at least one film therewithin, wherein said chamber is defined by a base, front wall, rear wall and a plurality of side walls of said cartridge, and wherein said front wall defines an opening to allow ejection of said single film, further wherein said base defines a slit along its longitudinal surface; and a tab assembly slidably engaged with said chamber, wherein said tab assembly comprises: a carrier strip defining a first surface to be mateably engaged with said at least one film and a second surface opposite to said first surface, wherein said carrier strip defines a film engagement arm extending at an angle relative to longitudinal axis of the carrier strip; and a tab affixed to said carrier strip at its second surface, said tab extending at an angle relative to the longitudinal axis of said carrier strip. In an embodiment, the cartridge further comprises a biasing member defined along a wall opposite to said base to urge said at least one film towards said carrier strip. In an embodiment, length of said carrier strip is short as compared to length of said at least one film. In an embodiment, the tab extends from the slit upon engagement of said tab assembly with said chamber. In an embodiment, the carrier strip is at an angle relative to longitudinal axis of said base. In an embodiment, the carrier strip is tapered towards said opening.

In an embodiment, the dispensing device can incorporate smart features to enable record keeping in respect of timing, dose size, frequency of doses and symptoms before and after a prescribed dose. The maintained records can help in allowing doctors and patients to gain a better understanding of how the medication is functioning to develop a customized treatment program. In an embodiment, the dispenser can incorporate a display screen configured to display symptoms before and after a prescribed dose has been administered to a patient.

In an embodiment, the dispensing device can further incorporate means to communicate data in real time or on as required basis to various stakeholders such as doctor, care giver, drug stores, pharmaceutical companies etc. The means for communication can be a wireless communication means that can enable data transfer from the dispenser to external functional units or networks. Communication between the dispenser and external functional units or networks may be accomplished through any suitable communication channels such as Bluetooth, Wi-Fi, GSM communication means such as 3G etc.

Figure 1:
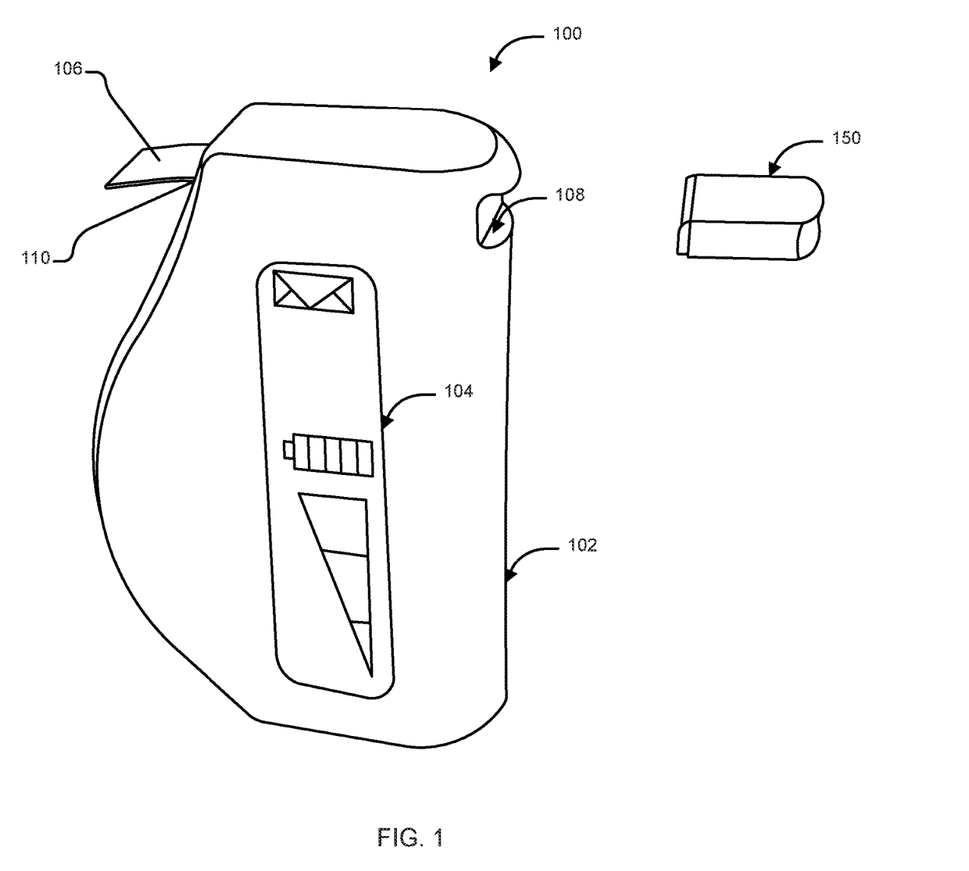
FIG. 1 illustrates an exemplary image 100 of the dispensing device, realized in accordance with an embodiment of the present disclosure.

FIG. 1 illustrates an exemplary image of the dispensing device 100, realized in accordance with an embodiment of the present disclosure. As shown in FIG. 1, the dispensing device 100 includes a housing 102 defining a dispensing orifice 110, and a slot 108 for receiving a cartridge 150 having stored therein at least one film containing a predetermined dosage of medication. The screen 104 provided on the dispensing device 100 can indicate status of Wi-Fi, GSM connectivity, effectiveness of medication dose and battery status. The screen 104 can be further used to display and/or enter different data and information that the dispensing device (alternatively referred to herein as dispenser) may provide or may be required to process or store. Also shown in the figure is a single film (alternatively referred as strip) 106 projecting out of the dispenser which a user can directly apply on his skin. Although few embodiments of the present disclosure are described herein with reference to transdermal films, a person skilled in the art would appreciate that the dispensing device of the present disclosure may find its utility for dispensation of a variety of articles such as film or layered products or consumables and all such applications are completely within the scope and spirit of the present invention.

Figure 2A:
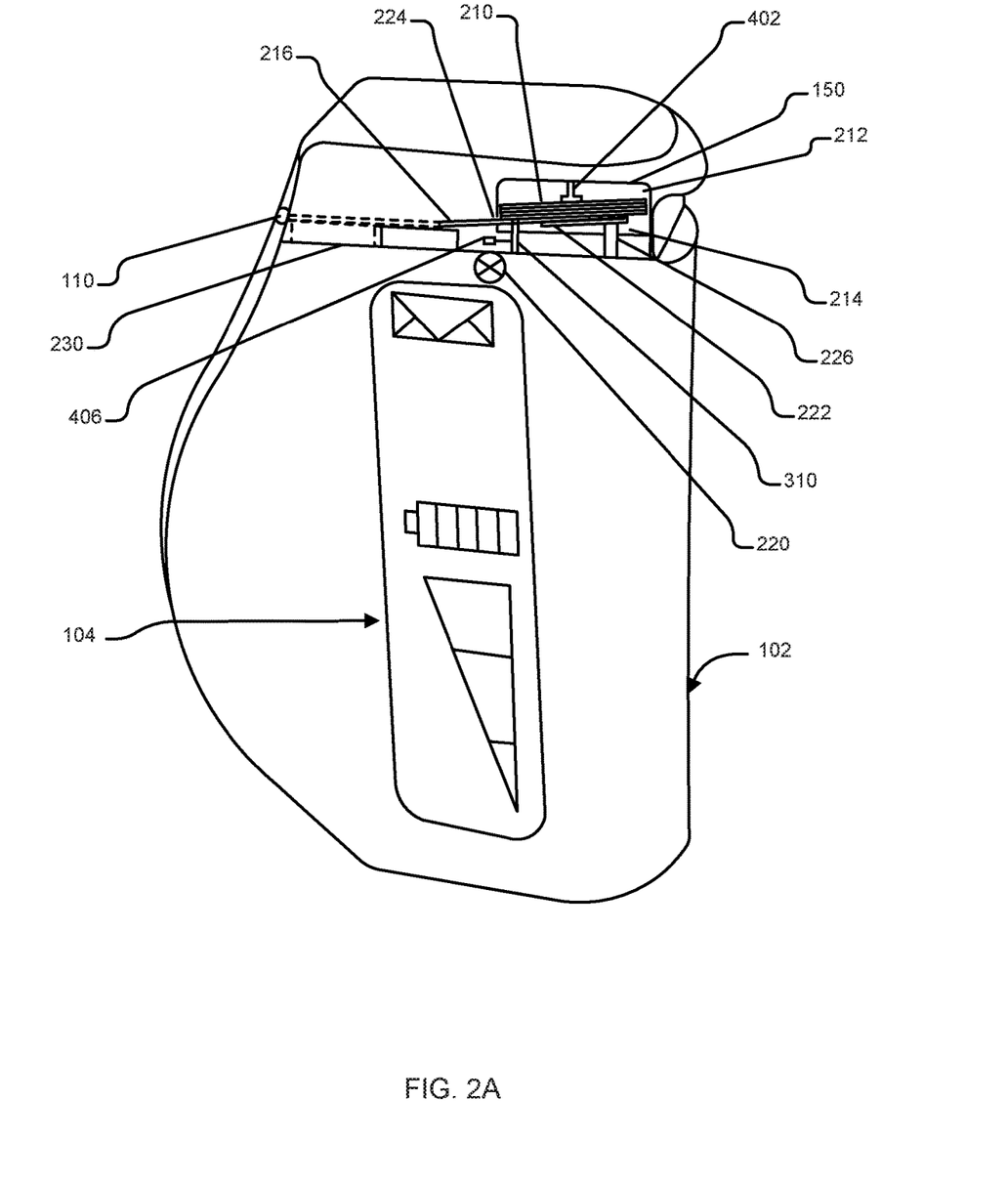
FIG. 2A illustrates an exemplary explored front view depicting various parts/elements of a dispensing device realized in accordance with an embodiment of the present disclosure.

FIG. 2A illustrates an exemplary explored front view depicting various parts/elements of a dispensing device realized in accordance with an embodiment of the present disclosure. As can be seen from FIG. 2A, the film dispensing device 100 includes a housing 102 defining a dispensing orifice 110, a cartridge 150 for storing one or a plurality of films 210, said cartridge including a chamber 212 to hold one or a plurality of films 210 therewithin and a tab assembly 214 slidably engaged with said chamber 212 and a driving unit 220 configured to engage with said tab assembly and a carrier strip 222. As can also be seen, the device includes a film carrier track 230 configured to convey the ejected film 216 from the opening 224 provided on cartridge to the dispensing orifice 110 of the dispensing device for dispensation thereof to a user. As can also be seen, the base of the cartridge includes a lug 310 to blockingly engage with said carrier strip to preclude movement thereof. Although the blocking member herein is described as lug, a person skilled in the art would appreciate that any other blocking member such as a ball, bearing, latch and the likes can be used to serve the purpose of blocking movement of the carrier strip as described in embodiments of the present disclosure without departing from the scope of the present disclosure. Normally, the lug 310 remains in the blocking state precluding forward movement of the carrier strip on account of provision of a biasing member coupled thereto. The biasing member can be any of a spring, tensioner and the like mechanisms as known to a person skilled in the art. Also shown is a lug engagement arm 406, configured as part of the dispensing device, that can movingly disengage the lug from said carrier strip allowing for movement of carrier strip in forward direction for ejection of a film. The lug engagement arm 406 can be configured as magnetic arm, mechanical arm or the like mechanisms, as known to or appreciated by a person skilled in the art, to serve its intended purpose as laid down in embodiments of the present disclosure. In an embodiment, the dispenser is configured to first authenticate the user. In an embodiment, the dispenser/dispensing device is in communication with a computing device. When the user requests for dispensation of the film, the dispensing device can authenticate the user. Alternatively, the computing device is configured to authenticate the user and then send signal to the dispensing device. In an embodiment, the dispenser/dispensing device is in communication with a computing device running thereon an app that can authenticate the user. Upon successful authentication, the lug engagement arm 406 movingly disengage the lug from said carrier strip allowing for movement of carrier strip in forward direction for ejection of a film.

Figure 2B:
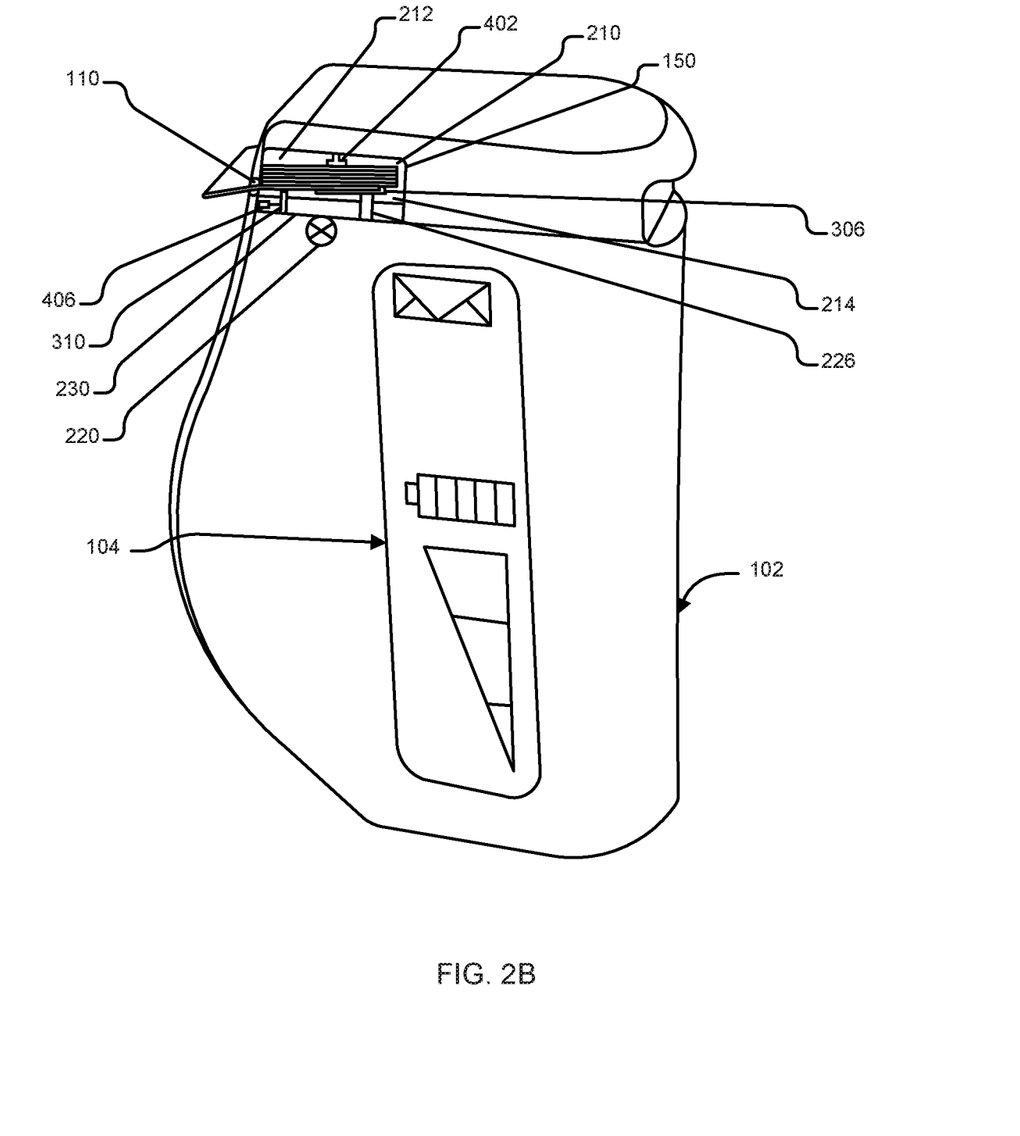
FIG. 2B illustrates an exemplary explored front view depicting various parts/elements of a variant of a dispensing device as illustrated in FIG. 2A, realized in accordance with an embodiment of the present disclosure.

FIG. 2B illustrates an exemplary explored front view depicting various parts/elements of a variant of a dispensing device as illustrated in FIG. 2A, realized in accordance with an embodiment of the present disclosure. As can be seen from FIG. 2B, the dispensing device includes a cartridge 150 placed in a position such that opening for ejection of a single film from the cartridge is in mating relationship with a dispensing orifice 110 of the dispenser allowing for ready/direct dispensation of said ejected single film from the dispensing orifice to a user.

Figure 3A:
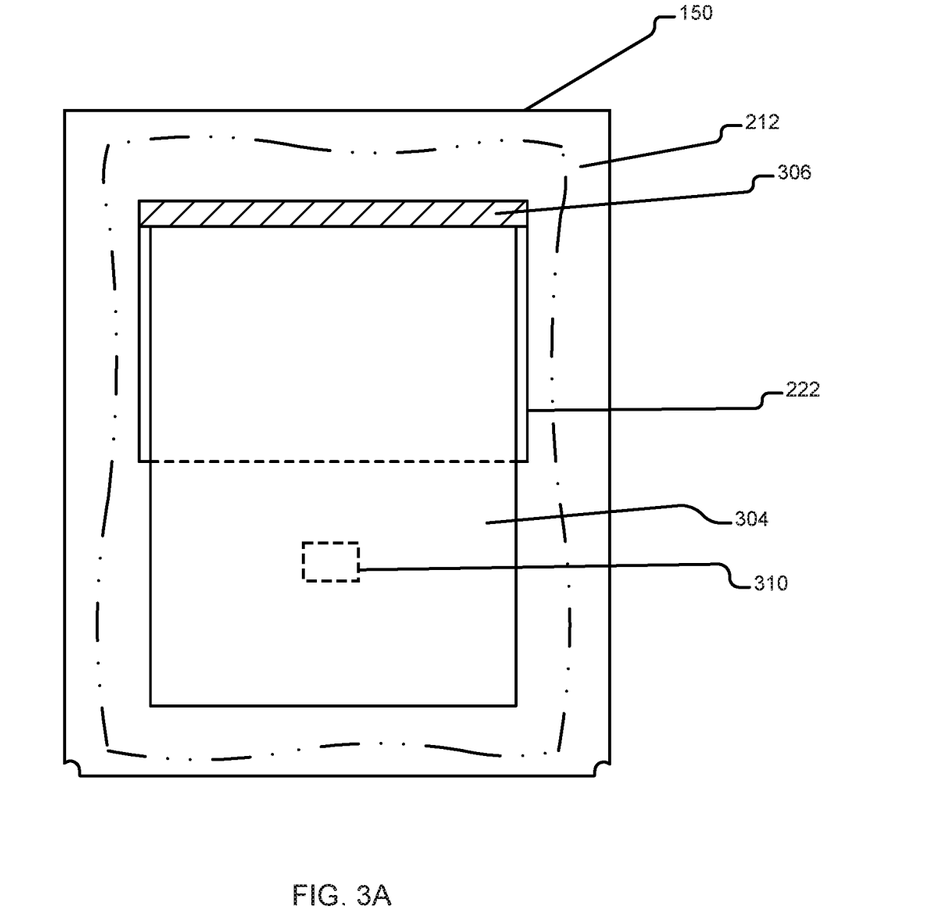
FIG. 3A illustrates an exemplary explored top view of the cartridge realized in accordance with an embodiment of the present disclosure.

FIG. 3A illustrates an exemplary exposed top view of the cartridge realized in accordance with an embodiment of the present disclosure. As illustrated, the cartridge includes a chamber 212 to hold one or a plurality of films 210 (a single film shown as 304) therewithin and a tab assembly including a carrier strip 222 defining a film engagement arm 306 extending at an angle relative to longitudinal axis of the carrier strip 222. The film engagement arm allows the tab assembly to grasp a single film that upon application of a force moves along the carrier strip to be ejected from the opening.

Figure 3B:
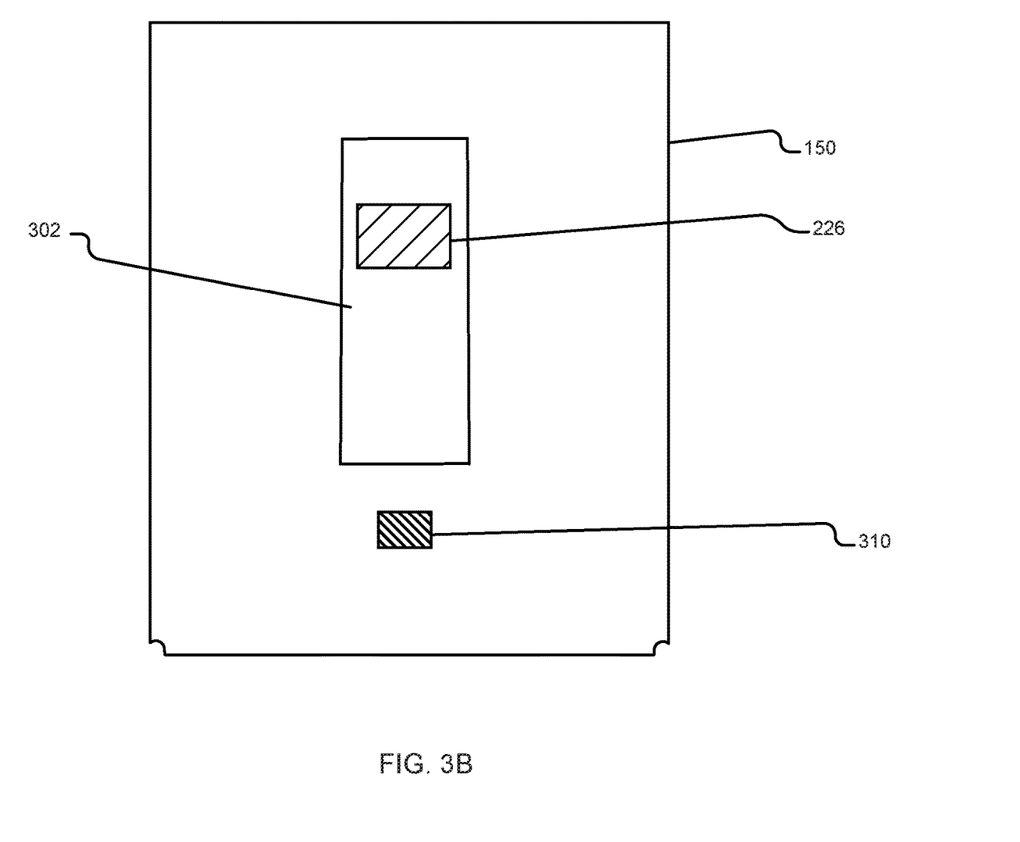
FIG. 3B illustrates an exemplary bottom view of the cartridge realized in accordance with an embodiment of the present disclosure.

FIG. 3B illustrates an exemplary bottom view of the cartridge realized in accordance with an embodiment of the present disclosure. As illustrated, the base or base wall of the cartridge 150 defines a slit 302 along its longitudinal surface to slidably engage tab 226 of the tab assembly 214 therewith. As can also be seen, the base further includes a lug 310 to blockingly engage with said carrier strip.

Figure 4:
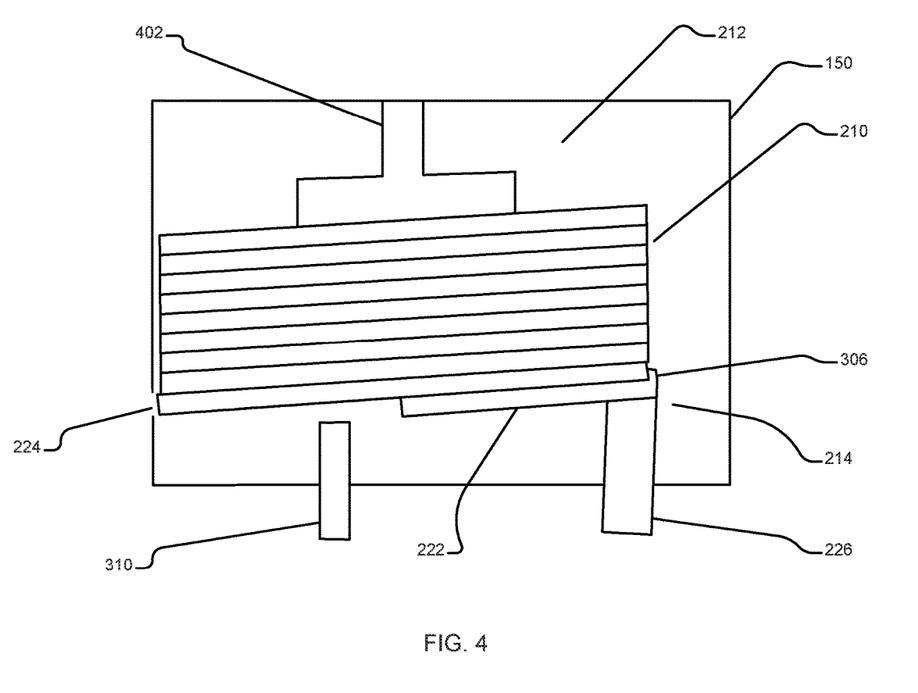
FIG. 4 illustrates an exemplary explored side view of the cartridge realized in accordance with an embodiment of the present disclosure.

FIG. 4 illustrates an exemplary exposed side view of the cartridge realized in accordance with an embodiment of the present disclosure. As can be seen, the cartridge includes a chamber to hold one or a plurality of films 210 therewithin, a tab assembly 214 slidably engaged with said chamber 212, said tab assembly including a carrier strip 222 defining a film engagement arm 306 extending at an angle relative to longitudinal axis of the carrier strip and a tab 226 affixed to said carrier strip, said tab 226 extending at an angle relative to the longitudinal axis of said carrier strip. As also can be seen, the cartridge further includes a biasing member 402 defined along a wall opposite to said base to urge said at least one film towards said carrier strip. The length of said carrier strip is short as compared to length of said the film. Further, the carrier strip is at an angle relative to longitudinal axis of said base. Preferably, the carrier strip is tapered towards said opening.

Figure 5:
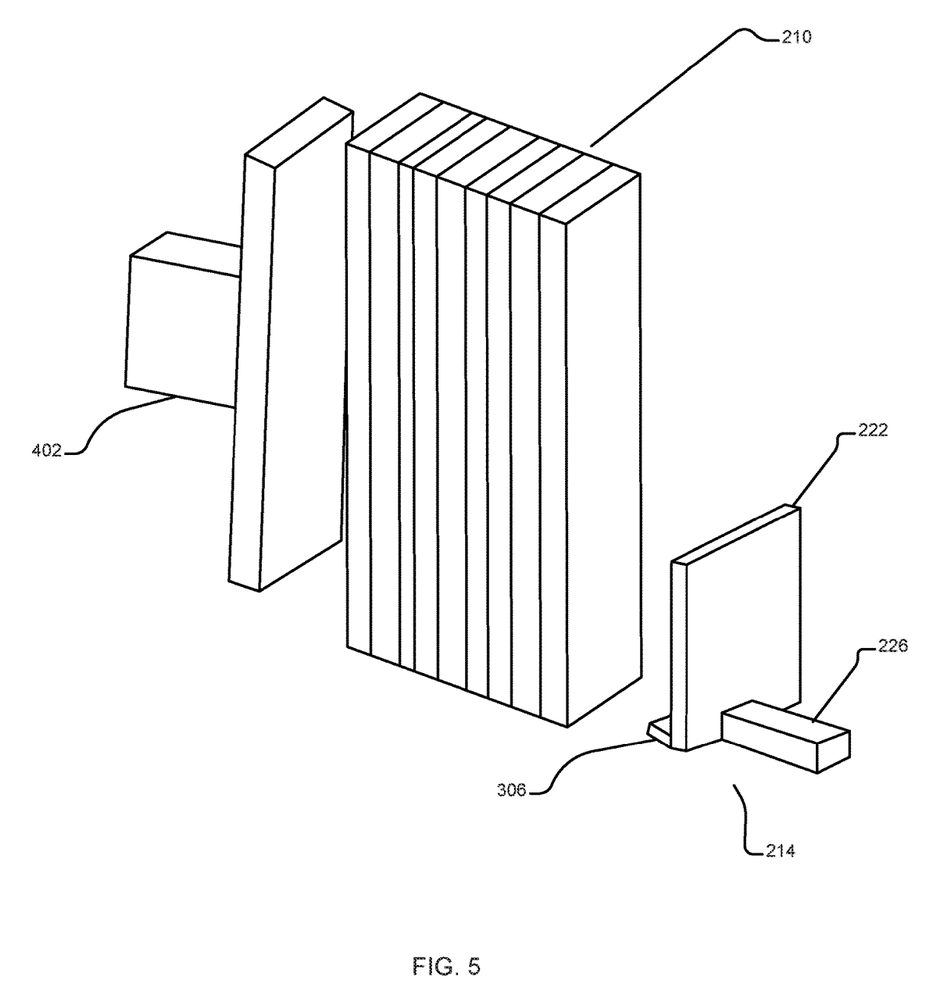
FIG. 5 illustrates an exemplary explored view depicting arrangement of the tab assembly and a biasing member in relation to the plurality of films stacked inside the cartridge, in accordance with an embodiment of the present disclosure.

FIG. 5 illustrates an exemplary exposed view depicting arrangement of the tab assembly and a biasing member in relation to the plurality of films stacked inside the cartridge, in accordance with an embodiment of the present disclosure.

Coming to operation of the dispensing device, the cartridge 150 is inserted in the slot 108 provided as part of the housing 102 of the device 100. Once, the cartridge is received inside the slot, the user can actuate the device for effecting removal of a single strip from the cartridge. On pressing the actuator or by providing command to said device to dispense the film (for example, from a computing device operatively coupled with the dispensing device through a smart film dispensation app), the lug engagement arm 406 movingly disengage the lug 310 from said carrier strip 222 allowing for movement of carrier strip in forward direction for ejection of a film. Once the lug 310 is disengaged or as the lug is being brought to a disengaged position, the driving unit 220, specifically, the tab engagement arm of the driving unit engages with the tab 226 affixed to the carrier strip. The motor 220 (or such other driving means) then moves the tab engagement arm along the track forcing the tab and the carrier strip affixed thereto to move along its longitudinal axis. The carrier strip having grasped a single film, using the film engagement arm 306 extending at an angle relative to longitudinal axis of the carrier strip, moves a single film towards the opening 224 provided at front wall of the cartridge. As the carrier strip moves to a second position (defining end of slot towards the opening end), the single film ejects from the opening. As a single film is ejected from the opening of cartridge, the biasing member 402 defined along a wall opposite to the base of the cartridge urges a second film (present on top of the film dispensed from the stack) towards the carrier strip making it ready for dispensation. In case the cartridge is engaged with the dispensing device as shown in FIG. 2A, wherein the opening of cartridge and the dispensation orifice of dispenser are in mating relationship, the single film is dispensed directly/readily to the user. In case the cartridge is engaged with the dispensing device as shown in FIG. 2B, wherein the opening of cartridge and the dispensation orifice of dispenser are not in mating relationship, as the carrier strip moves towards a second position, the film carrier track 230 initiates its movement towards the dispensation orifice. The ejected single film travel onto the film carrier track to be conveyed from the opening to the dispensing orifice 110 for dispensation thereof to the user. The sensor provided as part of the dispensing device, continuously monitors the ejected film for any discrepancies such film being physically damaged during its dispensation or if instead of single film, multiple films are ejected. In case of detection of any discrepancies, the sensor signals the controller of the dispensing device which in turn can take suitable corrective measures and/or flags the event to a computing device associated with the dispensing device.

According to embodiments of the present disclosure, the dispenser can be constructed such that it can be held and operated in one hand, and configured to dispense consistent and preselected single dosage lengths of drug containing strips in a ready-to-be-applied manner, thus providing a more precise dosage for treatment and avoiding unnecessary steps in the application of strip on a receiving surface such as a human skin.

Figure 6:
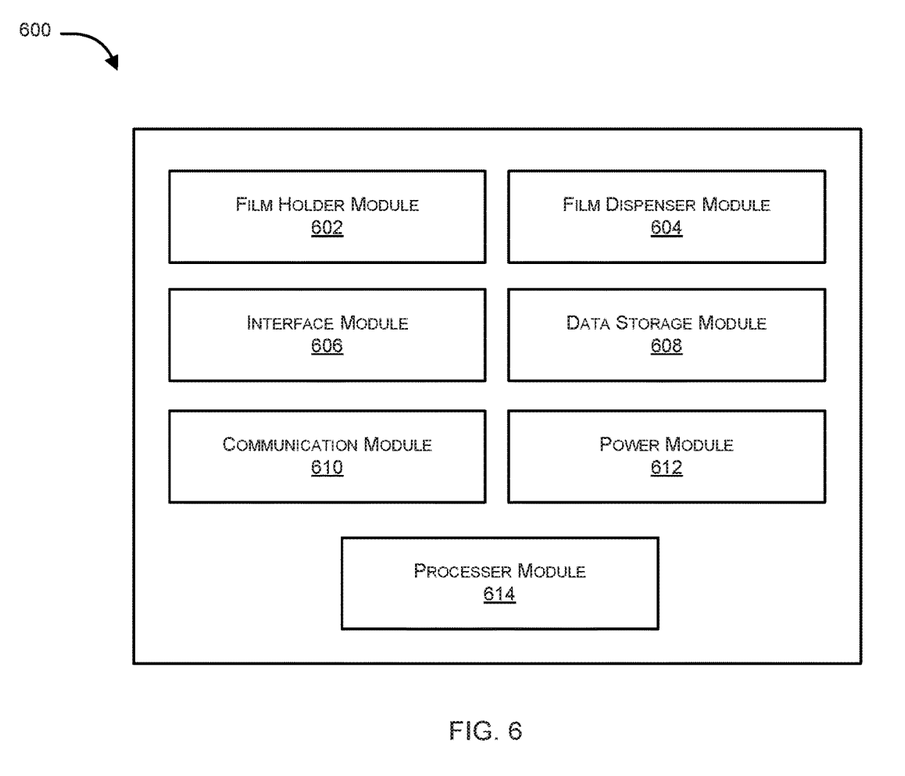
FIG. 6 that illustrates an exemplary block diagram indicating various functional subsystems of the disclosed dispensing device, realized in accordance with an embodiment of the present disclosure.

Referring now to FIG. 6 that illustrates an exemplary block diagram 600 indicating various functional subsystems of the disclosed dispenser. The dispenser 600 can include a film holder module 602, a film dispenser module 604, an interface module 606, a data storage module 608, a communication module 610, a power module 612 and a processer module 614.

In an embodiment, the film holder module 602 can be configured to hold a film carrying a pharmaceutical or herbal formulation for delivery in roll form or cartridge form. The roll or the cartridge can last for number of doses sufficient for few days thus enabling a user to carry his medicine requirement in a convenient manner. In an embodiment, the holder module 102 can be configured such that it forms a case to enclose and protect the roll or cartridge from contamination, and to provide for easy refilling of the dispenser. In an embodiment, the film can be formulated to have a controlled amount of transdermal medication per unit length, and the dosage of the medication along the length of the strip supply may be uniform. In an exemplary embodiment, the roll or cartridge can carry 50 doses. User if required can carry replacement rolls/cartridge to refill the dispenser. As can be seen, it provides hygienic storage without user having to touch the thin film strip.

In an alternative embodiment, the cartridge hold the film in form of a roll. The film dispenser module 604 can be configured to dispense precise length of the film from the roll or cartridge. The dispenser module 604 can include a measurement means for metering the length of transdermal strip dispensed, and a cutter for severing a length of transdermal strip from the roll or cartridge. Each strip so dispensed can then be directly applied to a receiving surface such as a human skin in a sterile and sanitary fashion with the use of a single hand. The film dispenser module 604 can precisely control length of the film thus maintaining a precise control on the medication dose. The free end of the strip can remain within the dispenser and can project out only when user activates the dispenser for taking next dose.

In an embodiment, the film dispenser module 604 can be configured to dispense a predetermined length of transdermal strip which determines the dose of transdermal medication or alternatively can be configured to vary the dose depending on symptoms or certain physiological parameters of the user.

In an embodiment, the interface module 606 can be configured to permit user to interact with the dispenser to observe medication dose history including timing, dose size, and frequency of doses, dose effectiveness, account settings, and the like and may also permit the user to control dose size, issue commands, to connect the dispenser with external functional units, and the like. In an embodiment, the interface module 606 can incorporate a touch screen for user to view and also enter different data and information that the dispenser may provide or may be required to process or store. In an exemplary embodiment, the interface module 606 can incorporate a touch screen that can be configured to display patient's symptoms before and after a dose has been delivered transdermally.

In an embodiment, the data storage module 608 can be configured to store information such as of timing, dose size, frequency of doses, symptoms and/or physiological parameters before and after a dose etc. The stored information can provide records to help doctors and patients to gain a better understanding of how the medication is functioning to develop a customized treatment program. It can also allow pharmaceutical and nutriceutical companies to learn about the effectiveness of their medicine after clinical trials and can further allow them to stay connected to the patients using their medicines to gather data and perform analytics.

In an embodiment, the communication module 610 can be configured to communicate data in real time or on as required basis to various stakeholders such as doctor, caregiver, drug stores, pharmaceutical companies etc. The means for communication can be a wireless communication means that can enable data transfer from the dispenser 100 to external functional units or networks such as, but not limited to computing devices, mobile devices, networks, databases, application software, etc. Communication between the dispenser 100 and external functional units or networks may be accomplished through any suitable communication channels such as, but not limited to, Bluetooth, Wi-Fi, GSM communication means such as 3G etc. Thus, the disclosed dispenser and an external functional system may communicate and provide information and/or instructions one to the other.

In an embodiment, the processer module 614 can be configured to control the function of the dispenser and the various modules and components thereof. In an exemplary embodiment, the processer module 614 can be configured to process digital data provided by user in respect of physiological parameters, symptoms etc. and based on pre-fed data provide dose to be administered.

In an embodiment, the power module 612 can be configured to meet power requirement of various functional subsystems of the dispenser. The power module 612 can comprise a rechargeable battery with connected charging port and charging circuit. In an exemplary embodiment, the battery once charged can last for up to 5 days.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

Advantages of the Invention

The present disclosure provides a film dispensing device that generally overcomes the deficiencies found in the conventional dispensing device.

The present disclosure provides a film dispensing device for dispensing of a film.

The present disclosure provides a film dispensing device for dispensing of a film impregnated with at least one active ingredient.

The present disclosure provides a film dispensing device capable of delivering an active agent in a controlled manner.

The present disclosure provides a film dispensing device capable of monitoring and electronically recording medication doses administered to a patient The present disclosure provides a cartridge for storing at least one film and dispensing a single film at a time.

The present disclosure provides a film dispensing device for dispensing of a film without any human intervention.

The present disclosure provides a film dispensing device capable of delivering an active agent without any overdose or under-dose.

The present disclosure provides a film dispensing device capable of delivering an active agent under sterile condition.

The present disclosure provides a film dispensing device capable of delivering an active agent without any gastro-intestinal discomfort.

The present disclosure provides a film dispensing device that is easy to operate.

The present disclosure provides a portable film dispensing device.

The present disclosure provides a film dispensing device that requires user approval for dispensing of a film.

I claim:

1. A film dispensing device, said device comprising:
   a housing defining a dispensing orifice;
   a cartridge for storing one or a plurality of films, said cartridge comprising:
      a chamber to hold said one or a plurality of films therewithin, said chamber defined by base, front wall, rear wall and a plurality of side walls of said cartridge, wherein said front wall defines an opening to allow ejection of a single film out of said one or a plurality of films, and wherein said base defines a slit along its longitudinal surface; and
      a tab assembly slidably engaged with said chamber, said tab assembly comprising:
         a carrier strip defining a film engagement arm extending at an angle relative to longitudinal axis of the carrier strip; and
         a tab affixed to said carrier strip, said tab extending at an angle relative to the longitudinal axis of said carrier strip; and
   a driving unit configured to engage with said tab assembly, wherein said driving unit, upon actuation, forces said tab to move along the slit to eject said single film from the opening,
   wherein said base further defines a lug to blockingly engage with said carrier strip precluding forward movement thereof.

2. The film dispensing device as claimed in claim 1, wherein said driving unit comprises a tab engagement arm, a track, and a motor.

3. The film dispensing device as claimed in claim 1, wherein said device further comprises a film carrier track configured to convey said ejected film from said opening to the dispensing orifice for dispensation thereof to a user.

4. The film dispensing device as claimed in claim 1, wherein said opening is matingly engaged with said dispensing orifice to allow dispensation of said ejected single film from the dispensing orifice.

5. The film dispensing device as claimed in claim 1, wherein said cartridge further comprises a biasing member defined along a wall opposite to said base to urge said one or a plurality of films towards said carrier strip.

6. The film dispensing device as claimed in claim 1, wherein length of said carrier strip is short as compared to length of said one or a plurality of films.

7. The film dispensing device as claimed in claim 1, wherein said carrier strip is at an angle relative to longitudinal axis of said base.

8. The film dispensing device as claimed in claim 1, wherein said carrier strip is tapered towards said opening.

9. The film dispensing device as claimed in claim 1, wherein said device further comprises a sensor configured to detect any or a combination of number of the ejected film and quality of the ejected film.

10. The film dispensing device as claimed in claim 1, wherein said device further comprises a lug engagement arm, that upon actuation of the device movingly disengage said lug from said carrier strip.

11. The film dispensing device as claimed in claim 1, wherein said one or a plurality of films comprises a multi-layered film.

12. The film dispensing device as claimed in claim 11, wherein said multi-layered film comprises any or a combination of a backing layer, a protective layer, an adhesive layer and a carrier layer.

13. The film dispensing device as claimed in claim 12, wherein said carrier layer comprises a film impregnated with any or a combination of at least one pharmaceutical agent, at least one herbal ingredient, at least one nutraceutical and at least one cosmetic agent.

14. A cartridge for storing one or a plurality of films and dispensing a single film at a time, said cartridge comprising:
   a chamber to hold said one or a plurality of films therewithin, wherein said chamber is defined by a base, front wall, rear wall and a plurality of side walls of said cartridge, and wherein said front wall defines an opening to allow ejection of said single film, further wherein said base defines a slit along its longitudinal surface; and
   a tab assembly slidably engaged with said chamber, wherein said tab assembly comprises:
      a carrier strip defining a first surface to be mateably engaged with said one or a plurality of films and a second surface opposite to said first surface, wherein said carrier strip defines a film engagement arm extending at an angle relative to longitudinal axis of the carrier strip; and a tab affixed to said carrier strip at its second surface, said tab extending at an angle relative to the longitudinal axis of said carrier strip, wherein said base further defines a lug to blockingly engage with said carrier strip precluding forward movement thereof.

15. The cartridge as claimed in claim 14, wherein said cartridge further comprises a biasing member defined along a wall opposite to said base to urge said one or a plurality of films towards said carrier strip.

16. The cartridge as claimed in claim 14, wherein length of said carrier strip is short as compared to length of said one or a plurality of films.

17. The cartridge as claimed in claim 14, wherein said tab extends from the slit upon engagement of said tab assembly with said chamber.

18. The cartridge as claimed in claim 14, wherein said carrier strip is at an angle relative to longitudinal axis of said base.

19. The cartridge as claimed in claim 14, wherein said carrier strip is tapered towards said opening.

* * * * *